US005780283A

United States Patent [19]

Lee

[11] Patent Number: 5,780,283

[45] Date of Patent: Jul. 14, 1998

[54] ENZYME STABILIZATION BY OXYGEN-CONTAINING BLOCK COPOLYMERS

[75] Inventor: James C. Lee, Memphis, Tenn.

[73] Assignee: Buckman Laboratories International, Inc., Memphis, Tenn.

[21] Appl. No.: 528,610

[22] Filed: Sep. 15, 1995

Related U.S. Application Data

[63] Continuation of Ser. No. 160,865, Dec. 3, 1993, abandoned.

[51] Int. Cl.[6] .............................. C12N 9/96; C11D 7/42; C11D 3/386

[52] U.S. Cl. .............................. 435/188; 510/305; 510/321; 510/393; 510/530

[58] Field of Search .............................. 435/188; 510/305, 510/321, 393, 530

[56] References Cited

U.S. PATENT DOCUMENTS

| | | | |
|---|---|---|---|
| 3,078,315 | 2/1963 | Steele, Jr. et al. | 568/625 |
| 3,676,373 | 7/1972 | Paviak | 252/531 |
| 3,950,133 | 4/1976 | Monte et al. | 436/66 |
| 4,064,010 | 12/1977 | Harris et al. | 435/191 |
| 4,169,817 | 10/1979 | Weber | 252/545 |
| 4,243,543 | 1/1981 | Guilbert et al. | 252/105 |
| 4,243,546 | 1/1981 | Shaer | 252/174.12 |
| 4,261,868 | 4/1981 | Hora et al. | 252/529 |
| 4,266,031 | 5/1981 | Tang et al. | 435/188 |
| 4,305,837 | 12/1981 | Kaminsky et al. | 252/174.12 |
| 4,318,818 | 3/1982 | Letton et al. | 252/174.12 |
| 4,381,247 | 4/1983 | Nakagawa et al. | 252/95 |
| 4,404,115 | 9/1983 | Tai | 252/135 |
| 4,443,355 | 4/1984 | Murata et al. | 252/174.12 |
| 4,462,922 | 7/1984 | Boskamp | 252/174.12 |
| 4,490,285 | 12/1984 | Kebanii | 252/551 |
| 4,529,525 | 7/1985 | Dormal et al. | 252/132 |
| 4,537,707 | 8/1985 | Severson, Jr. | 252/545 |
| 4,537,764 | 8/1985 | Pellico et al. | 424/50 |
| 4,548,727 | 10/1985 | Shaer | 252/171 |
| 4,801,544 | 1/1989 | Munk | 435/188 |
| 4,842,758 | 6/1989 | Crutzen | 252/817 |
| 4,906,396 | 3/1990 | Falholt et al. | 252/174.12 |
| 4,908,150 | 3/1990 | Hessel et al. | 252/174.12 |
| 4,914,031 | 4/1990 | Zukowski et al. | 435/222 |
| 5,071,586 | 12/1991 | Kaiserman et al. | 252/174.12 |
| 5,073,292 | 12/1991 | Hessel et al. | 252/174.12 |
| 5,082,585 | 1/1992 | Hessel et al. | 252/174.12 |
| 5,108,735 | 4/1992 | Ohtsuki et al. | 424/50 |
| 5,124,066 | 6/1992 | Russell | 252/174.12 |
| 5,156,773 | 10/1992 | Kochavi et al. | 252/174.12 |
| 5,169,553 | 12/1992 | Durbut et al. | 252/99 |
| 5,270,194 | 12/1993 | D'Alterio et al. | 435/188 |

FOREIGN PATENT DOCUMENTS

| | | |
|---|---|---|
| 0 352 244 A2 | 1/1990 | European Pat. Off. . |
| 0385526 | 2/1990 | European Pat. Off. . |
| 629692 | 6/1994 | European Pat. Off. . |
| 286181 | 1/1991 | German Dem. Rep. . |
| 4065494 | 3/1992 | Japan . |
| 5025491 | 2/1993 | Japan . |

*Primary Examiner*—Jon P. Weber

*Attorney, Agent, or Firm*—Armstrong, Westerman, Hattori, McLeland & Naughton

[57] ABSTRACT

A method for stabilizing an enzyme against decomposition at elevated temperatures or by water is described which comprises combining the enzyme with stabilizing amounts of a non-ionic polyether-polyol block-copolymer surfactant. Stabilized compositions based on the enzyme and surfactant are also described.

29 Claims, No Drawings

ENZYME STABILIZATION BY OXYGEN-CONTAINING BLOCK COPOLYMERS

This application is a continuation of application Ser. No. 08/160,865, filed Dec.3, 1993, now abandoned.

FIELD OF THE INVENTION

The field of the invention is the stabilization of enzymes by means of a non-ionic polyether-polyol block-copolymer surfactant.

DESCRIPTION OF RELATED ART

Enzymes generally are formulated into aqueous-based liquid enzymatic compositions designed for a particular process. These liquid enzymatic compositions, however, have historically been plagued with problems such as chemical instability which can result in the loss of enzymatic activity, particularly upon storage. This critical problem of loss of enzymatic activity upon storage has particularly affected the liquid detergent industry.

It is not uncommon to have industrial products, such as liquid enzymatic compositions, stored in warehouses in various climates around the world where the product is subjected to a temperature that may range from freezing to above 50° C. for extended periods. After storage at temperature extremes ranging from 0° C. to 50° C. for many months, most liquid enzymatic compositions lose from 20 to 100 percent of their enzymatic activity due to enzyme instability.

Various attempts have been made to stabilize enzymes contained in liquid enzymatic compositions. Attempts to increase the stability of liquid enzymatic compositions using formulations containing alcohols, glycerols, dialkylglycolethers, and mixtures of these and other compounds have had only marginal success, even in moderate storage temperature ranges.

In Munk, U.S. Pat. No. 4,801,544, a system of ethylene glycol and ethoxylated linear alcohol non-ionic surfactant with hydrocarbon solvent was utilized as a stabilizer and the encapsulation of enzymes in micelles within the solvent/surfactant mixture was described. The water content of the composition was kept at less than 5 percent, and enzyme stability was checked at 35°, 70° and 100° F.

The stabilization of an aqueous enzyme preparation using certain esters has been described by Shaer in U.S. Pat. No. 4,548,727. The ester used as a stabilizer has the formula, RCOOR', where R is an alkyl of from one to three carbons or hydrogen, and R' is an alkyl of from one to six carbons. The ester is present in the aqueous enzyme preparation in an amount from 0.1 to about 2.5% by weight. The enzyme ingredient that is employed according to the patentee is a commercial enzyme preparation sold in a dry powder, solution or slurry form containing from about 2 percent to about 80 percent of active enzymes and a carrier such as sodium or calcium sulfate, sodium chloride, glycerol, non-ionic surfactants or mixtures thereof as the remaining 20 percent to 98 percent.

Letton et al., U.S. Pat. No. 4,318,818 describes a stabilizing system for aqueous enzyme compositions where the stabilizing system comprises calcium ions and a low molecular weight carboxylic acid or its salt. The pH of the stabilizing system is from about 6.5 to about 10.

Guilbert et al., U.S. Pat. No. 4,243,543 teaches the stabilization of liquid proteolytic enzyme-containing detergent compositions. The detergent compositions are stabilized by adding an antioxidant and a hydrophilic polyol to the composition while stabilizing the pH of the composition.

Weber, U.S. Pat. No. 4,169,817 teaches a liquid cleaning composition containing stabilized enzymes. The composition is an aqueous solution containing from 10% to 50% by weight of solids and including detergent builders, surface active agents, an enzyme system derived from *Bacillus subtilus* and an enzyme stabilizing agent. The stabilizing agents comprise highly water soluble sodium or potassium salts and/or water soluble hydroxy alcohols and enable the solution to be stored for extended periods without de-activation of the enzymes.

Dorrit et al., European Patent No. 0 352 244 A2 describes stabilized liquid detergent compositions using an amphoteric surfactant.

Kaminsky et al., U.S. Pat. No. 4,305,837 describes stabilized aqueous enzyme compositions containing a stabilizing system of calcium ions and a low molecular weight carboxylic acid or salt and a low molecular weight alcohol. This stabilized enzyme is used in a detergent composition. The composition may include non-ionic surfactants having the formula $RA(CH_2CH_2O)_nH$ where R is a hydrophobic moiety, A is based on a group carrying a reactive hydrogen atom and n represents the average number of ethylene oxide moieties. R typically contains from about 8 to about 22 carbon atoms but can be formed by the condensation of propylene oxide with a lower molecular weight compound whereas n usually varies from about 2 to about 24. The low molecular weight alcohol employed may be either a monohydric alcohol containing from 1 to 3 carbon atoms or a polyol containing from 2 to about 6 carbon atoms and from 2 to about 6 hydroxy groups. Kaminsky et al. note that the polyols can provide improved enzyme stability and include propylene glycol, ethylene glycol and glycerine.

Tai, U.S. Pat. No. 4,404,115 describes an aqueous enzymatic liquid cleaning composition which contains as an enzyme stabilizer, an alkali metal pentaborate, optionally with an alkali metal sulfite and/or a polyol. The polyol contains 2–6 hydroxy groups and includes materials such as 1,2-propane diol, ethylene glycol, erythritan, glycerol, sorbitol, mannitol, glucose, fructose, lactose, and the like.

Boskamp, U.S. Pat. No. 4,462,922 also describes an aqueous enzymatic detergent composition with a stabilizer based on a mixture of boric acid or a salt of boric acid with a polyol or polyfunctional amino compound together with a reducing alkali metal salt. Substantially the same polyols are used as in Kaminsky et al.

Accordingly, the present invention is directed to a method for providing stabilized enzymes and a stabilized enzyme composition in which the foregoing and other disadvantages are overcome. The advantages sought according to the present invention are to provide a novel method for stabilizing enzymes as well as a stabilized enzyme composition.

SUMMARY OF THE INVENTION

Accordingly, the present invention is directed to a novel method and composition that substantially obviates one or more of the foregoing and other problems due to limitations and disadvantages of the related art.

Additional features and advantages of the invention will be set forth in the description which follows, and in part will be apparent from the description, or may be learned by practice of the invention. The advantages of the invention will be realized and obtained by the method and composition of matter, particularly, pointed out in the written description and claims hereof.

To achieve these and other advantages and in accordance with the purpose of the invention, as embodied and broadly described, a novel method for stabilizing an enzyme against loss of activity at elevated temperatures or by water is set forth comprising combining the enzyme with a stabilizing amount of a non-ionic polyether-polyol block-copolymer surfactant.

Where the enzyme is stabilized against deactivation at elevated temperatures the surfactant is selected to have a cloud point greater than such temperatures.

In one embodiment, the non-ionic polyether-polyol block-copolymer surfactant is a polyoxyalkylene glycol ether all-block, block-heteric, heteric-block or heteric-heteric block copolymer where the alkylene units have from 2 to about 4 carbon atoms and especially those surfactants which contain hydrophobic and hydrophilic blocks where each block is based on at least oxyethylene groups or oxypropylene groups or mixtures of these groups.

The invention also comprises a composition of matter based on the foregoing enzyme and surfactant.

It is to be understood that both the foregoing general description and the following detailed description are exemplary and explanatory and are intended to provide further explanation of the invention as claimed.

DETAILED DESCRIPTION OF THE INVENTION

The present invention is directed to a method for stabilizing an enzyme against loss of activity, either at elevated temperatures or by water, by combining the enzyme with a non-ionic polyether-polyol block-copolymer surfactant.

The use of enzymes and liquid enzymatic compositions in industry and in the commercial marketplace has grown rapidly over the last several years. As is well-known, enzymes can be acid, alkaline or neutral, depending upon the pH range in which they are active. All of these types of enzymes are contemplated to be useful in connection with the invention disclosed herein.

Many enzymes and liquid enzymatic compositions have been associated with liquid detergents and have shown utility as solubilizing and cleaning formulations. In addition to their association with liquid detergents, enzymes and liquid enzymatic compositions have also shown utility in a number of different commercial and industrial areas in which a wide variety of enzyme Proteases are a well-known class of enzymes frequently utilized in a wide variety of industrial applications where they act to hydrolyze peptide bonds in proteins and proteinaceous substrates. Commercially, the greatest uses of proteases are made in the laundry detergent industry, where they help to remove protein based stains such as blood or egg stains, and in the cheese making industry, where they aid in curdling milk. Proteases are also used as meat tenderizers, for softening leather, for modifying food ingredients, and for flavor development. Liquid enzymatic compositions containing alkaline proteases have also shown to be useful as dispersants of bacterial films and algal and fungal mats in cooling tower waters and metalworking fluid containment bays.

Proteases can be characterized as acid, neutral, or alkaline proteases depending upon the pH range in which they are active. The acid proteases include the microbial rennets, rennin (chymosin), pepsin, and fungal acid proteases. The neutral proteases include trypsin, papain, bromelain/ficin, and bacterial neutral protease. The alkaline proteases include subtilisin and related proteases. Commercial liquid enzymatic compositions containing proteases are available under the names Rennilase®, "PTN" (Pancreatic Trypsin NOVO), "PEM" (Proteolytic Enzyme Mixture), Neutrases®, Alcalase®, Esperase®, and Savinase™ which are all supplied by Novo Nordisk Bioindustrials, Inc. of Danbury, CT. Another commercial protease is available under the name HT-Proteolytic supplied by Solvay Enzyme Products.

Amylases, another class of enzymes, have also been utilized catalyze or accelerate the hydrolysis of starch. Amylases are used largely in the corn syrup industry for the production of glucose syrups, maltose syrups, and a variety of other more refined end products of starch hydrolysis such as high fructose syrups. As a class they include α-amylase, β-amylase, amyloglucosidase (glucoamylase), fungal amylase, and pullulanase. Commercial liquid enzymatic compositions containing amylases are available under the names BAN, Termamyl®, AMG, Fungamyl®, and Promozyme™, which are supplied by Novo Nordisk, and Diazyme L-200, a product of Solvay Enzyme Products.

Other commercially valuable enzyme classes are those which affect the hydrolysis of fiber. These classes include cellulases, hemicelluloses, pectinases, and β-glucanases. Cellulases are enzymes that degrade cellulose, a linear glucose polymer occurring in the cell walls of plants. Hemicelluloses are involved in the hydrolysis of hemicellulose which, like cellulose, is a polysaccharide found in plants. The pectinases are enzymes involved in the degradation of pectin, a carbohydrate whose main component is a sugar acid. β-glucanases are enzymes involved in the hydrolysis of β-glucans which are also similar to cellulose in that they are linear polymers of glucose. In a commercial context, these enzymes have utility to a greater or lesser degree in manufacturing processes dependent on fiber degradation.

Cellulases have reported utility in the de-inking process of old newsprint (ONP) wastepaper, eliminating the need for any surfactants and alkaline chemicals. The enzymes dislodge inks from fiber surfaces and disperse ink particles to a finite size. See S. Say-Kyoun Ow, *Biological De-Inking Methods of Newsprint Wastepaper*, World Pulp and Paper Technology, pp. 63, 64 (1992). Collectively, cellulases include endocellulase, exocellulase, exocello-biohydrolase, and cellobiase. Commercial liquid enzymatic compositions containing cellulases are available under the names Celluclast® and Novozym®188 which are both supplied by Novo Nordisk.

Hemicelluloses are also used in the de-inking process to dislodge ink particles from the fiber surface of ONP. See D. Y. Prasad et al., *Enzyme Deinking of Black and White Letterpress Printed Newsprint Waste*, Progress in Paper Recycling, May 1992, pp. 21, 22. Additionally, hemicelluloses, such as the xylanases, are employed in the pulp bleaching process. Xylanase pretreatment of kraft pulps has resulted in major reductions in bleaching chemical requirements, such as molecular chlorine, and has also improved pulp quality as reflected by higher brightness ceilings. See D. J. Senior et al., *Reduction in Chlorine Use During Bleaching of Kraft Pulp Following Xylanase Treatment*, Tappi Journal (forthcoming publication; aspects of the publication were presented at the 1991 International Pulp Bleaching Conference, Stockholm). PULPZYM® product, available from Novo Nordisk, and ECOPULP® product, from Alko Biotechnology, are two examples of commercially available liquid enzymatic compositions containing xylanase-based bleaching enzymes.

As a class, hemicelluloses include hemicellulose mixture and galactomannanase. Commercial liquid enzymatic compositions containing hemicelluloses are available as PULPZYMX® from Novo, ECOPULP® from Alko Biotechnology and Novozym®280 and Gamanase™, which are both products of Novo Nordisk.

The pectinases are used commercially to weaken cell walls and enhance extraction of fruit juice, as well as to aid in decreasing viscosity and preventing gelation in these extracts. Pectinases consist of endopolygalacturonase, exopolygalacturonase, endopectate lyase (transeliminase), exopectate lyase (transeliminase), and endopectin lyase (transeliminase). Commercial liquid enzymatic compositions containing pectinases are available under the names Pectinex™Ultra SP and Pectinex™*, both supplied by Novo Nordisk.

The β-glucanases play an important role in the malting and brewing industries where modification of barley cell walls containing β-glucans is necessary. β-glucanases are comprised of lichenous, laminarinase, and exoglucanase. Commercial liquid enzymatic compositions containing p-glucanases are available under the names Novozym®234, Cereflo®, BAN, Finizym®, and Ceremixt®, all of which are supplied by Novo Nordisk.

Two additional classes of industrially and commercially useful enzymes are lipases and phospholipases. Lipases and phospholipases are esterase enzymes which hydrolyze fats and oils by attacking the ester bonds in these compounds. Lipases act on triglycerides, while phospholipases act on phospholipids. In the industrial sector, lipases and phospholipases represent the commercially available esterases, and both currently have a number of industiral and commercial applications.

In the pulp and paper industry, liquid enzyme preparations containing lipases have proven to be particularly useful in reducing pitch deposits on rolls and other equipment during the production process. For example, the treatment of unbleached sulfite pulp with lipases prior to bleaching with chlorine to reduce the content of chlorinated triglycerides, which are reportedly the cause of pitch deposition during the paper manufacturing process, has been reported. See K. Fischer and K. Messner, *Reducing Troublesome Pitch in Pulp Mills By Lipolytic Enzymes*, Tappi Journal, February 1992, p. 130. Novo Nordisk markets two liquid lipase preparations under the names Resinase™ A and Resinase™A 2X, both of which, under certain conditions, reportedly reduce pitch deposits significantly by breaking down wood resins in pulp.

Another important use of lipases is to degrease hides and pelts in the leather making process. Alkaline lipases are used in conjunction with special proteases and emulsifying systems to aid degreasing, as well as to improve the soaking and liming effect in leather making. See J. Christner, *The Use of Lipases in the Bea mouse Processes*, 87 J.A.L.C.A. 128 (1992).

Lipases have also been used for the development of flavors in cheese and to improve the palatability of beef tallow to dogs. In nonaqueous systems, lipases have been employed to synthesize esters from carboxylic acids and alcohols.

Commercial liquid enzymatic compositions containing lipases are available. For example, such compositions are available under the trade names Lipolase 100, Greasex 50L, Palatase™A, Palatase™, and Lipozyme™ which are all supplied by Novo Nordisk.

With respect to the commercially useful phospholipases, pancreatic phospholipase $A_2$ has been used to convert lecithin into lysolecithin. Lysolecithin reportedly is an excellent emulsifier in the production of mayonnaise and the baking of bread. Commercially, phospholipase $A_2$ is available in a liquid enzymatic composition sold as LECITASE™ by Novo Nordisk.

Another commercially valuable class of enzymes are the isomerases which catalyze conversion reactions between isomers of organic compounds. The isomerases are particularly important in the high fructose corn syrup industry. For example, the aldoseketose isomerase reaction, catalyzed by glucose isomerase, involves the conversion of glucose to fructose and is just one of three key enzyme reactions in the industry. Sweetzyme™ product is a liquid enzymatic composition containing glucose isomerase which is supplied by Novo Nordisk.

Redox enzymes are enzymes that act as catalysts in chemical oxidation/reduction reactions and, consequently, are involved in the breakdown and synthesis of many biochemicals. Currently, many redox enzymes have not gained a prominent place in industry since most redox enzymes require the presence of a cofactor. However, where cofactors are an integral part of an enzyme or do not have to be supplied, redox enzymes are commercially useful, particularly in the food processing industry.

The redox enzyme, glucose oxidase, is used to prevent unwanted browning reactions affecting food color and flavor. Glucose oxidase is also used as an "oxygen scavenger" to prevent the development of off-flavors in juices and to preserve color and stability in certain sensitive food ingredients. The redox enzyme, catalase, has been utilized to decompose residual hydrogen peroxide used as a sterilizing agent. A third redox enzyme, lipoxidase (lipoxygenase), found naturally in soya flour and not usually purified for industrial use, is used in baking, not only to obtain whiter bread, but also to reverse the dough softening effects caused by certain agents. Other redox enzymes have possible applications ranging from the enzymatic synthesis of steroid derivatives to use in diagnostic tests. These redox enzymes include peroxidase, superoxide dismutase, alcohol oxidase, polyphenol oxidase, xanthine oxidase, sulfhydryl oxidase, hydroxylases, cholesterol oxidase, laccase, alcohol dehydrogenase, and steroid dehydrogenases.

Of the various non-ionic polyether-polyol surfactant block-copolymers available, the preferred materials comprise polyoxyalkylene glycol ethers which contain hydrophobic and hydrophilic blocks, each block being based on at least oxyethylene groups or oxypropylene groups or mixtures of these groups.

The most common method of obtaining these surfactants is by reacting ethylene oxide with the hydrophobic material which contains at least one reactive hydrogen. Alternative routes include the reaction of the hydrophobe with a preformed polyglycol or the use of ethylene chlorohydrin instead of ethylene oxide.

The reacting hydrophobe must contain at least one active hydrogen as in the case of alcohols, acids, amides, mercaptans, and the like. Primary amines can be used as well.

Especially preferred non-ionic surfactants are those obtained by block polymerization techniques. By the careful control of monomer feed and reaction conditions, a series of surfactants can be prepared in which such characteristics as the hydrophile-lipophile balance (HLB), wetting and foaming power can be closely and reproducibly controlled. The chemical nature of the initial component employed in the formation of the initial polymer block generally determines the classification of the surfactants. The initial component does not have to be hydrophobic since hydrophobicity will be derived from one of the two polymer blocks. Typical starting materials or initial components include monohydric alcohols such as methanol, ethanol, propanol, butanol and the like as well as dihydric materials such as glycol, glycerol, higher polyols, ethylene diamine and the like.

The various classes of preferred surfactants, suitable for practice of the present invention have been described by Schmolka in "Non-Ionic Surfactants," Surfactant Science Series Vol. 2, Schick, M.J., Ed. Marcel Dekker, Inc., New York, 1967, Chapter 10 which is incorporated herein by reference. The first and simplest is that in which each block is homogeneous which is to say a single alkylene oxide is used in the monomer feed during each step in the preparation. Such materials are referred to as all-block surfactants. The next classes are termed block-heteric and heteric-block, in which one portion of the molecule (i.e., either the hydrophobe or hydrophile) is composed of a single alkylene oxide while the other is a mixture of two or more such materials, one of which may be the same as that of the homogeneous block portion of the molecule. In the preparation of such materials, the hetero portion of the molecule will be totally random. The properties of these non-ionics will be entirely distinct from those of the pure block surfactants. The other subclass is that in which both steps in the preparation of the hydrophobe and hydrophile involve the addition of mixtures of alkylene oxides and is defined as a heteric-heteric block copolymer.

The block polymer surfactant is typified by a monofunctional starting material such as a monohydric alcohol, acid, mercaptan, secondary amine or N-substituted amide employed as the initiator. Such materials can generally be illustrated by the following formula:

$$I-[A_m-B_n]_x$$

where I is the starting material molecule as described before. The A portion is a hydrophobe comprising an alkylene oxide unit in which at least one hydrogen has been replaced by an alkyl group or an aryl group, and m is the degree of polymerization which is usually greater than about 6. The B moiety is an aqueous solubilizing group such as oxyethylene with n again being the degree of polymerization. The value of x is the functionality of I. Thus, where I is a monofunctional alcohol or amine, x is 1; where I is a polyfunctional starting material such as a diol (e.g., propylene glycol) x is 2 as is the case with the Pluronic® surfactants. Where I is a tetrafunctional starting material such as ethylenediamine, x will be 4 as is the case with Tetronic® surfactants. Preferred surfactants of this type are the polyoxypropylene-polyoxyethylene block copolymers.

Multifunctional starting materials may also be employed to prepare the homogeneous block surfactants.

In the block-heteric and heteric-block materials either A or B will be a mixture of oxides with the remaining block being a homogeneous block. One block will be the hydrophobe and the other the hydrophile. Either of the two polymeric units will serve as the solubilizing unit but the characteristics will differ depending on which is employed. Multifunctional starting materials can also be employed in materials of this type.

The heteric-heteric block copolymers are prepared essentially the same way as discussed previously with the major difference being that the monomer feed for the alkylene oxide in each step is composed of a mixture of two or more materials. The blocks will therefore be random copolymers of the monomer feed with the solubility characteristics determined by the relative ratios of potentially water soluble and water insoluble materials.

The average molecular weight of the polyoxyalkylene glycol ether block copolymers utilized according to the present invention is from about 500 to about 30,000 especially from about 800 to about 25,000 and preferably from about 1,000 to about 12,000. The weight ratio of hydrophobe to hydrophile will also vary from about 0.4:1 to 2.5:1, especially from about 0.6:1 to about 1.8:1 and preferably from about 0.8:1 to about 1.2:1.

In an especially preferred embodiment, these surfactants have the general formula:

$$RX(CH_2CH_2O)_nH$$

where the hydrophobe of the block copolymer has an average molecular weight of from about 500 to about 2,500, especially from about 1,000 to about 2,000 and preferably from about 1,200 to about 1,500 and where R is usually a typical surfactant hydrophobic group but may also be a polyether such as a polyoxypropylene group or a mixture of polyoxypropylene and polyoxyethylene groups. In the above formula X is either oxygen or nitrogen or another functionality capable of linking the polyoxyethylene chain to the hydrophobe. In most cases, n, the average number of oxyethylene units in the hydrophilic group, must be greater than about 5 or about 6 to impart sufficient water solubility to make the materials useful.

The polyoxyalkylene glycol ethers are the preferred non-ionic polyether-polyol block-copolymer surfactants. However, other non-ionic block-coplymer surfactants useful is the invention can be modified block copolymers using the following as starting materials: (a) alcohols, (b) fatty acids, (c) alkylphenol derivatives, (d) glycerol and its derivatives, (e) fatty amines, (f)-1,4-sorbitan derivatives, (g) castor oil and derivatives, and (h) glycol derivatives.

Cloud point is one of the most distinct characteristics for most non-ionic surfactants and depends on the number of oxyethylene, oxypropylene, and/or oxybutylene groups reacted in the formation of the surfactant block copolymers of the present invention. Cloud point is also affected by other components in solution, the concentration of surfactants, and the solvents, if any, in the system. Cloud point has been defined as the sudden onset of turbidity of a non-ionic surfactant solution on raising the temperature. When the non-ionic surfactant is dissolved in water, it is theorized that an increase of temperature will increase the activity of the water molecules, which cause the dehydration of ether oxygens in the polyoxyethylene group in the non-ionic surfactant. Molecules with greater percentages of oxyethylene groups have a greater capacity for hydration, and so have a higher cloud point. This is important in the stabilization of enzymes in solution, since the long-term stability of the enzyme is evaluated at a temperature of 50° C. If the cloud point of a non-ionic surfactant is less than 50° C., when the solution reaches that temperature, the enzyme will hydrate while the surfactant has coalesced and becomes less water soluble.

Cloud point has also been described as that characteristic of the non-ionic surfactants in which they exhibit an inverse temperature-solubility relationship in water, which is to say that as the temperature of the solution is increased, the solubility of the surfactant decreases. This phenomenon has been attributed to a disruption of specific interactions such as hydrogen bonding between the water and the polyoxyethylene units in the molecule. The temperature at which components of the polyoxyethylene surfactant begin to precipitate from solution is defined as the "cloud point " In general, the cloud point of the given family of surfactants will increase with the average number of oxyethylene groups.

The cloud point of the non-ionic polyether-polyol surfactant block copolymers and especially the polyoxyalkylene glycol ether surfactant polymers of the present invention is greater than the temperature at which the enzyme or enzyme system degrades and may be anywhere from about 0° C. to about 110° C., especially from about 10° C. to about 100° C. and preferably from about 20° C. to about 95° C. These cloud points are for a 1 weight % solution of the surfactant in water.

Although the inventor does not want to be limited by any theory, it is believed that the non-ionic surfactants of the present invention contribute to the stability of the enzyme by increasing the viscosity of the water in the formulation. Generally, high viscosity will lead to poor transport to the Ca++ rich zones in enzymes such as protease, or slower ion transfer. This also helps to keep the matrix of the enzyme intact, although in some of the cases described according to the present invention, the higher viscosity may not be necessary for stability.

Chelating agents generally deactivate enzymes, thereby decreasing the molecular compactness of the enzyme, causing deformation of the enzyme and thereby inactivating it. Non-ionic surfactants are not influenced by the electrostatic effect, i.e., by the charged groups on the enzyme, and so do not impact on the special structure of the enzyme.

A suitable polyoxyalkylene glycol ether block-copolymer that may be used according to the present invention contains a hydrophobe based on a hydrocarbon moiety of an aliphatic monohydric alcohol containing from 1 to about 8 carbon atoms, where the hydrocarbon moiety has attached thereto through an ether oxygen linkage, a heteric mixed chain of oxyethylene and 1,2-oxypropylene groups. The weight ratio of oxyethylene groups to 1,2-oxypropylene groups in the hydrophobe is from about 5:95 to about 15:85 and the average molecular weight of the hydrophobe is from about 1,000 to about 2,000. A hydrophile is attached to the mixed chain and is based on oxyethylene groups. The weight ratio of hydrophile to hydrophobe is anywhere from about 0.8:1 to about 1.2:1. This polyoxyalkylene glycol ether is further defined by Steele, Junior, et al., U.S. Pat. No. 3,078,315 which is incorporated herein by reference.

One of the preferred polyoxyalkylene glycol ethers is Tergitol XD produced according to the method of Steele, Jr., et al. U.S. Pat. No. 3,078,315 and available from Union Carbide. This is a non-ionic block copolymer having a cloud point of about 76° C. as a 1% solution in water and a molecular weight of about 3120 based on its hydroxyl number. Other non-ionic polyoxyalkylene glycol ether block-copolymers can be employed such as those manufactured by the BASF Wyandotte Corporation including Pluronic® and Tetronic® types. Pluronic® and Tetronic® polyol surfactants vary from mobile liquids to flakable solids and those with high ethylene oxide contents exhibit no solution cloud point even at 100° C. Other similar non-ionic polyoxyalkylene glycol ether block-copolymer surfactants can be employed such as those manufactured by Dow Chemical Company and Witco Chemical Corporation.

The Pluronic® surfactants that may also be employed according to the present invention are prepared by synthesizing a hydrophobe of desired molecular weight by the controlled addition of propylene oxide to the two hydroxyl groups of propylene glycol. Ethylene oxide is then added to both ends of the hydrophobe to form oxyethylene chains that constitute from about 10 wt. % to about 80 wt. % of the final molecule. The average molecular weight of the Pluronic® surfactant is from about 1,100 to about 12,600 and the HLB (hydrophobe lipophobe balance) is from about 1–7 to about 18–23 or greater than about 24. Pluronic® P-105 employed according to the present invention has an average molecular weight of about 6,500, a melting point of about 35° C., a cloud point of about 91° C. and an HLB of about 12–18. Tetronics surfactants that may also be employed according to the invention are tetra-functional block copolymers derived from the sequential addition of propylene oxide and then ethylene oxide to ethylenediamine. The average molecular weight of these surfactants is from about 1,650 to about 30,000 and have an HLB of from about 1–7 to about 18–23 and greater than about 24. Tetronic® 1304 employed according to the invention has an average molecular weight of about 10,500, a melting point of about 59° C., a cloud point greater than about 100° C. and an HLB greater than about 24.

In one embodiment, the method of the invention comprises stabilizing an enzyme having from about 1 to about 90% by weight of water based on said enzyme and said water by means of the aforesaid non-ionic polyether-polyol block-copolymer surfactant. The invention also comprises a stabilized enzyme composition containing from about 1 to about 90% by weight of water based on the aforesaid enzyme and water in combination with the aforesaid non-ionic polyether-polyol block-copolymer surfactant.

The enzyme and surfactant may also be used in combination with an organic solvent compatible with the enzyme and which will also act as a solvent for the non-ionic polyether-polyol block-copolymer surfactant. The solvent preferably is hydrophilic such as a polyol or a mixture of polyols where the polyol has from 2 to about 6 carbon atoms and from 2 to about 6 hydroxyl groups and includes materials such as 1,2-propane diol, ethylene glycol, erythritan, glycerol, sorbitol, mannitol, glucose, fructose, lactose, and the like.

The stabilized enzyme composition according to the present invention, therefore may contain an enzyme in an amount from about 2 to about 95 parts by weight, especially from about 5 to about 90 parts by weight and preferably from about 10 to about 80 parts by weight, water in an amount from about 1 to about 90 parts by weight and especially from about 2 to about 85 parts by weight and preferably from about 5 to about 80 parts by weight, a solvent from about 0 to about 70 parts by weight and especially from about 2 to about 60 parts by weight and preferably from about 3 to about 55 parts by weight and the non-ionic polyether-polyol block-copolymer surfactant in an amount from about 0.2 to about 40 parts by weight and especially from about 0.8 to about 30 parts by weight and preferably from about 1 to about 25 parts by weight.

The following examples are illustrative.

EXAMPLE 1

The composition listed below was made from Pulpzyme HB, an aqueous enzyme suspension, commercially available from Novo Nordisk Bioindustrials, Inc. which is a xylanase preparation with a bacterial origin. Tergitol XD, as described above was also employed. The glycerol used is a 96% pure material where the impurity is water. A higher purity glycerol may also be employed. The glycerol acts as a solvent for Tergitol XD, which is a solid at room temperature. Viscosity of the formulation is 2,200 cps measured, by using a Brookfield viscosimeter model LVT, at 30 rpm, spindle number 4 at room temperature (20° C.). The formulation dissolves easily in water. Enzyme activity, IU per ML, was measured according to the method of Bailey, M.J. et al., *J. Biotech* 23, 257–270, 1992. This method entails a five-minute incubation of the xylanase enzyme (suitably diluted in pH 5.3 citrate buffer) with a 1% birchwood xylan substrate. After incubation, the released sugars are determined by a 5 minute reaction with the original DNS reagent of Sumner (1921). Absorbance is measured at 540 nm against a reagent blank comprised of substrate, DNS reagent and buffer. Enzyme readings are corrected by subtracting an enzyme blank composed of substrate and DNS reagent to which the diluted enzyme is added with immediate color development/quenching rather than incubation.

| Component | Weight Percent |
|---|---|
| Pulpzyme HB | 75 |
| Glycerol | 5 |
| Tergitol XD | 20 |

Table 1 below shows the excellent stability of this formulation. The enzyme activity increase is within experimental error.

TABLE 1

| Enzyme Stabilization In Example 1 Enzyme Activity (IU per ML)* | | | |
|---|---|---|---|
| Original Sample | Room Temperature | 8° C. | 50° C. |
| 9170 | 9130 | 9820 | 10900 |

*Thirty days at the condition indicated.

EXAMPLE 2

Example 1 was repeated using Pulpzyme HB, however, Tergitol XD was substituted by Pluronic® P-105which is a commercial non-ionic block copolymer available from BASF Wyandotte Corporation. The cloud point of this copolymer is 91° C. (1% solution in water) and 940° C. (10% solution in water). The average molecular weight of the surfactant is about 6,500.

Table 2 shows, within experimental error, the reduction in stability of this formulation when compared to Example 1 which appears to be a function of Pluronice® P-105 compared to Tergitol XD. Stability is nonetheless better than enzymes without Pluronic® P-105. The enzyme will rapidly lose its activity under these conditions without the stabilization provided by Pluronic® ®P-105.

TABLE 2

| Enzyme Stabilization In Example 2 Enzyme Activity (IU per ML)* | | | |
|---|---|---|---|
| Original Sample | Room Temperature | 8° C. | 50° C. |
| 8400 | 8280 | 8970 | 7370 |

*Thirty days at the condition indicated.

EXAMPLE 3

Example 1 was repeated using a protease enzyme from Solvay Enzymes, Inc. or a lipase enzyme from Novo Nordisk Bioindustrials, Inc., the results of which are set forth in Table 3.

TABLE 3

| Component | Weight % | |
|---|---|---|
| HT-Proteolytic L-175 ® (protease) | 70 | 100 |
| Glycerol (96% plus) | 20 | |
| Tergitol XD | 10 | |
| Activity (14 days) | | |
| at 50° C. | 45 | 24 |
| at Room Temp. (20° C.) | 90 | 91 |

| Component | Weight % | | | |
|---|---|---|---|---|
| Resinase A2X ™ (lipase) | 85 | 85 | 85 | 85 |
| Glycerol (96% plus) | 5 | — | 5 | 5 |
| Tergitol XD | 10 | — | — | — |
| Water | — | 15 | — | — |
| Pluronic ® P105 | — | — | 10 | — |
| Tetronic 1304 ® | — | — | — | 10 |
| BASF Wyandotte | | | | |
| Activity (30 days) | | | | |
| at 50° C. | 0.049 | 0.033 | 0.047 | 0.0553 |
| at Room Temp. (20° C.) | 0.048 | 0.067 | 0.054 | 0.0472 |

It will be apparent to those skilled in the art that modifications and variations can be made in the method and composition of the present invention without departing from the spirit or scope thereof. It is intended that these modifications and variations and their equivalents are to be included as part of this invention provided they come within the scope of the appended claims.

What is claimed is:

1. A method for stabilizing an enzyme composition containing greater than about 20 weight percent of water against loss of activity evaluated at 50° C. comprising combining said enzyme with stabilizing amounts of a surfactant where the surfactant comprises:

a) a block polymer surfactant formed from a starting material having the formula:

$I-[A_m-B_n]_x$, wherein I represents an alcohol, A represents a hydrophobe comprising an alkylene oxide unit in which at least one hydrogen has been replaced by an alkyl group or an aryl group, m is the degree of polymerization which is greater than about 6, B is an aqueous solubilizing group comprising at least one oxyethylene group, n is the degree of polymerization which is greater than about 6, and x is the functionality of I and is from 1 to 4: or b) a surfactant having the formula:

$RO(CH_2CH_2O)_nH$, wherein R is a hydrophobic group, and n is greater than about 5.

2. The method of claim 1, wherein said enzyme is stabilized against decomposition at elevated temperatures by said surfactant which has a cloud point greater than said temperatures.

3. The method of claim 2, wherein said temperatures are from about 0° C. to about 100° C.

4. The method of claim 2, wherein said surfactant is dissolved in an organic solvent compatible with said enzyme.

5. The method of claim 1, wherein said enzyme is a system of an enzyme in combination with water, said enzyme being stabilized against decomposition from water by said non-ionic polyether-polyol block-copolymer-surfactant which raises the viscosity of water in said system.

6. The method of claim 5, wherein said surfactant is dissolved in an organic solvent compatible with said enzyme.

7. The method of claim 4 or 6, wherein said solvent is hydrophilic.

8. The method of claim 7, wherein said solvent is a polyol or a mixture of polyols.

9. The method of claim 8, wherein said polyol has from 2 to about 6 carbon atoms and from 2 to about six hydroxyl groups.

10. The method of claim 1, wherein said surfactant contains hydrophobic and hydrophilic blocks based on at least oxyethylene groups, oxypropylene groups or mixtures of said groups.

11. An enzyme composition containing greater than about 20 weight percent of water stabilized against loss of activity evaluated at 50° C. amount of a surfactant where the surfactant comprises:

a) a block polymer surfactant formed from a staring material having the formula:

$I-[A_m-B_n]_x$, wherein I represents an alcohol, A represents a hydrophobe comprising an alkylene oxide unit in which at least one hydrogen has been replaced by an alkyl group or an aryl group, m is the degree of polymerization which is greater than about 6, B is an aqueous solubilizing group comprising at least one oxyethlene group, n is the degree of polymerization which is greater than about 6, and x is the functionality of I and is from 1 to 4: or b) a surfactant having the formula:

$RX(CH_2CH_2O)_nH$, wherein R is a hydrophobic group, X is oxygen, and n is greater than about 5.

12. The composition of claim 11, wherein said enzyme is a system of an enzyme in combination with water, said enzyme being stabilized against decomposition from water by said non-ionic surfactant which raises the viscosity of water in said system.

13. The composition of claim 12, wherein said surfactant is dissolved in an organic solvent compatible with said enzyme.

14. The composition of claim 11, wherein said surfactant is dissolved in an organic solvent compatible with said enzyme.

15. The composition of claim 14 or 13, wherein said solvent is hydrophilic.

16. The composition of claim 15, wherein said solvent is a polyol or mixture of polyols.

17. The composition of claim 16, wherein said polyol has from 2 to about 6 carbon atoms and from 2 to about 6 hydroxyl groups.

18. The composition of claim 17 comprising an aqueous enzyme suspension of xylanase, said surfactant and glycerol.

19. The composition of claim 14 where said surfactant is a polyoxyalkylene glycol ether block-copolymer having a hydrophobe based on a hydrocarbon moiety of an aliphatic monohydric alcohol containing from 1 to about 8 carbon atoms, where the hydrocarbon moiety has attached thereto through an ether oxygen linkage, a heteric mixed chain of oxyethylene and 1,2-oxypropylene groups, the weight ratio of oxyethylene groups to 1,2-oxypropylene groups in the hydroprobe is from about 5:95 to about 15:85 and the average molecular weight of the hydrophobe is from about 1,000 to about 2,000, a hydrophile being attached to the mixed chain and is based on oxyethylene groups, and the weight ratio of hydrophile to hydrophobe is from about 0.8:1 to about 1.2:1.

20. The composition of claim 29 optionally including as a solvent, a polyol having from 2 to about 6 carbon atoms and from 2 to about 6 hydroxyl groups.

21. The composition of claim 20 wherein said solvent is glycerol and said enzymes are amylase, protease or lipase.

22. The composition of claim 14 where said surfactant is a polyoxyalkylene glycol ether block-copolymer having a hydrophobe based on a propylene oxide adduct of propylene glycol where the propylene glycol has attached thereto through an ether oxygen linkage, oxypropylene groups, a hydrophile being attached to the hydrophobe and is based on oxyethylene groups, the average molecular weight of the surfactant is from 1,100 to about 12,600, and the HLB is from about 1–7 to greater than about 24.

23. The composition of claim 33 optionally including as a solvent, a polyol having from 2 to about 6 carbon atoms and from 2 to about 6 hydroxyl groups.

24. The composition of claim 23 wherein said solvent is glycerol and said enzymes are amylase, protease or lipase.

25. The composition of claim 14 where said surfactant is a polyoxyalkylene glycol ether block-copolymer having a hydrophobe based on a propylene oxide adduct of ethylene diamine where the ethylenediamine has attached thereto through an ether oxygen linkage, 1,2-oxypropylene groups, a hydrophile being attached to the mixed chain and is based on oxyethylene groups, the average molecular weight of the surfactant is from about 1,650 to about 30,000, and the HLB is from about 1–7 to greater than about 24.

26. The composition of claim 37 optionally containing as a solvent, a polyol having from 2 to about 6 carbon atoms and from 2 to about 6 hydroxyl groups.

27. The composition of claim wherein said solvent is glycerol and said enzymes are amylase, protease or lipase.

28. The composition of claim 11, wherein said surfactant contains hydrophobic and hydrophilic blocks, each block being based on at least oxyethylene groups, or oxypropylene groups or mixtures of said groups.

29. The composition of claim 28, wherein the average molecular weight of said surfactant is from about 500 to about 30,000, the weight ratio of hydrophobe to hydrophile is from about 0.4:1 to about 2.5:1 and the cloud point of said surfactant is from about 0° C. to about 100° C.

* * * * *

UNITED STATES PATENT AND TRADEMARK OFFICE

CERTIFICATE OF CORRECTION

PATENT NO. : 5,780,283

DATED : July 14, 1998

INVENTOR(S) : James C. LEE

It is certified that error appears in the above-identified patent and that said Letters Patent is hereby corrected as shown below:

| | |
|---|---|
| In claim 5, line 4, | delete "non-ionic polyether-polyol block-copolymer". |
| In claim 11, line 3, | after "50° C." insert --where said composition comprises an enzyme in combination with a stabilizing--. |
| In claim 12, line 4, | delete "non-ionic". |
| In claim 20, line 1, | delete "29" and insert --19--. |
| In claim 23, line 1, | delete "33" and insert --22--. |
| In claim 26, line 1, | delete "37" and insert --25--. |
| In claim 27, line 1, | after "claim", insert --26--. |

Signed and Sealed this

Seventeenth Day of November, 1998

Attest:

BRUCE LEHMAN

*Attesting Officer*

*Commissioner of Patents and Trademarks*